United States Patent
Simpson et al.

(10) Patent No.: US 10,253,330 B2
(45) Date of Patent: *Apr. 9, 2019

(54) CLDN5 MINI-PROMOTERS

(71) Applicant: The University of British Columbia, Vancouver (CA)

(72) Inventors: Elizabeth M. Simpson, Vancouver (CA); Wyeth W. Wasserman, Vancouver (CA); Daniel Goldowitz, Port Moody (CA); Charles de Leeuw, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 356 days.

This patent is subject to a terminal disclaimer.

(21) Appl. No.: 14/180,003

(22) Filed: Feb. 13, 2014

(65) Prior Publication Data

US 2015/0024498 A1    Jan. 22, 2015

Related U.S. Application Data

(60) Provisional application No. 61/764,445, filed on Feb. 13, 2013.

(51) Int. Cl.
| | | |
|---|---|---|
| *C07H 21/02* | (2006.01) | |
| *C12N 15/63* | (2006.01) | |
| *C12N 5/00* | (2006.01) | |
| *A01K 67/00* | (2006.01) | |
| *C12N 15/85* | (2006.01) | |
| *C07K 14/705* | (2006.01) | |

(52) U.S. Cl.
CPC .......... *C12N 15/85* (2013.01); *C07K 14/705* (2013.01); *C12N 2830/008* (2013.01)

(58) Field of Classification Search
None
See application file for complete search history.

(56) References Cited

U.S. PATENT DOCUMENTS 6,884,598 B2    4/2005  Dougall
8,598,331 B2 *  12/2013  Simpson et al. ............ 536/24.1

2004/0151700 A1    8/2004  Harlan et al.
2009/0018031 A1    1/2009  Trinklein et al.
2011/0097803 A1 *  4/2011  Simpson et al. ............ 435/455

OTHER PUBLICATIONS

Brody, Functional Elements in Patent Claims, as Construed by the Patent Trial and Appeal Board (PTAB), Functional Elements in Patent Claims, as Construed by the Patent Trial and Appeal Board (PTAB), 2014, pp. 251-320.*
Burek; et al. "Cloning and characterization of the murine claudin-5 promoter", Mol Cell Endoncrinol (Jan. 2009), 298(1-2):19-24.
Chen; et al. "Brain capillary endothelial cells express MBEC1, a protein that is related to the Clostridium perfringens enterotoxin receptors", Lab Invest (Mar. 1998), 78(3):353-363.
Felinski; et al. "Glucocorticoids induce transactivation of tight junction genes occludin and claudin-5 in retinal endothelial cells via a novel cis-element", Exp Eye Res (Jun. 2008), 86(6):867-878.
Maynard; et al. "A comprehensive analysis of 22q11 gene expression in the developing and adult brain", PNAS USA (Nov. 2003), 100(24):14433-14438.
Matter; et al. "Holey barrier: claudins and the regulation of brain endothelial permeability", J Cell Biol (May 2003), 161(3):459-460.
Morita; et al. "Endothelial claudin: claudin-5/TMVCF constitutes tight junction strands in endothelial cells", J Cell Biol (Oct. 1999), 147(1):185-194.
Nitta; et al. "Size-selective loosening of the blood-brain barrier in claudin-5-deficient mice", J Cell Biol (May 2003), 161(3):653-660.
Stamatovic; et al. "Brain endothelial cell-cell junctions: how to "open" the blood brain barrier", Curr Neuropharmacol (Sep. 2008), 6(3):179-192.

* cited by examiner

*Primary Examiner* — Maria Marvich
(74) *Attorney, Agent, or Firm* — Pamela J. Sherwood; Bozicevic, Field & Francis LLP (57) ABSTRACT

Isolated polynucleotides comprising a CLDN5 mini-promoter are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The mini-promoter may also be provided in a vector, for example in combination with an expressible sequence. The polynucleotides find use in a method of expressing a sequence of interest, e.g. for identifying or labeling cells, monitoring or tracking the expression of cells, etc.

7 Claims, 1 Drawing Sheet

Specification includes a Sequence Listing.

US 10,253,330 B2

SEQUENCE LISTING

<160> NUMBER OF SEQ ID NOS: 4

<210> SEQ ID NO 1
<211> LENGTH: 2963
<212> TYPE: DNA
<213> ORGANISM: Artificial Sequence
<220> FEATURE:
<223> OTHER INFORMATION: synthetic nucleic acid sequence

<400> SEQUENCE: 1

```
ttttttttct cgttttactc acaaatactt aagtatgtaa gtagatacac ttcacccaca      60
taatagagaa tactctatac atgtattcat gggtcaaagg ggtccctgag atacacacaa     120
```

```
ttcatactca tccctctgaa cactgcaagc gtcgtgtgga gccatttgct ttcccacaca    180
ctcgctttct gccgcagcaa ggctggaccc tgctggagtg gtgatgtgca ggaactgcct    240
catagctcag gtggtaaagt tatttggctg ggaactgagt ctctcccac atgctgtcac     300 acccttcccg gccctgacaa acacaaagag atgcatccca ttgagtcacc cacttggctg    360
aaccgtgtac ctggtaacct ccttgggagg ttctttggag ggtattttc tcctctacac     420 aaagcatgcc tgcgaagtaa gctgagaatg acaaaaacag gaaagcccaa tcttgcagag    480
acagaggggc caaggcctgc atgataatgc ggcccaaatt catagctcag acccaaaaga    540
aaacaaatgt tccattcttt ctgtgtccac ctctaaacta gcaatacag tgagggcagt      600 aaattgcaat tacaagtaag aactttagca gttgctgatc ataaaatgaa aagggacaaa    660
tatgtttatc cttaacaggg tcacaaataa ttccacagct gttaattttg gcagccacga    720
ctctgcaggc agtatgggct catggtatac tatcttcatt gtcaccttgg acaaagatcc    780
tgttggccaa aggcacacag gcatcttcag gaaaactaga tttaaatggt aagattacct    840
atgcttatgt ttttaagctc caaagactac tggttctggg aaggactggg tcactatgtg    900
accttgtgta ggtctctttt ggccctgagt ccaggagggc tctgtgactc caggttgtgg    960
ctgcgtctgg cagctaacaa ttgtttagtt tacagtgtcc ttcctcttca tcttgtttgc    1020
attcagttgc ccatgcctgc ctctgggggg aggtgggaag gaatgtggct cctgggagga    1080
gcccagctcc atgtgccatt ctgaggagcc aggctgcacg cccctgggcc atagctgctg    1140
gtggatggat gagtacactg gcagaggcac tgggaaggga agacagaatt gttggccaat    1200 agtcccctt tactgatttt cttgtcattt ttgtgtttgt tttattataa agataacagc     1260
tgtatttgag aaagaaagct caaactataa agaaaattta aaattgccct gtcttactcc    1320
aactccattc cctgactagg tgagccagac gctggcctta tctcatttac catctcagag    1380
ccatctgaag gggagaagg gaaccgggcc ccaggaggga gaaagtcatc aaacctccca     1440
catctgtgac cagcctcagt gccatacttt ttctatggag ggccctgtcc aatggaactg    1500
agcacagacc agataaaaga actgggcacc cagtggcctc agtccagggc ctggagttca    1560
aactttactg gaaacaaagg ggccgagaga gactgggaa agaactacta gaaagggct      1620 ggtgccccca tggggctgtg ggttttggag ccgcgtgccc ccacctgagc ctcaggggc     1680 ccggagtgtc cacaccagtg gacctttcga gaaatggctg ggccattgtg cagaagaatg    1740
cccggaaatc ccgcgcctcc ctcctccagc aaggatgggg gctcttcctc ctggccagga    1800
aactccaagt tggcttccgg agggtggcct ggggggctggg gtgccaggga caccatcgcc   1860
actggtggga gggcagggca cagcccctcc gtgtcccttt gtctctcctg tctgaaggcc    1920
agagcaggct gctaggcctg gggccaccac tgccccctggg tgctacaccc agtgtgctgg   1980
gtcactggga acttcctgaa gtggtgtcac ctgaactgga ccccaagga tggggtgcgg     2040 gcagtaccgc aggaagagga gcagcccctg tgaagattga gaggtctggg aagcccctgc    2100
ggcttgggag agtgggggtc gccaggcagg gggaaagccc ctgtgccacc gcttttgcc     2160 agagactcag gctccagaga ggcagtgagt ggcatggggg gtgaggctgg ggccctgggc    2220
ctgacctcca cacgcctgcc tggcctctct gtttgccatg ggatgagaga gacagtgctg    2280
ggactcagag cggggctgga gagtgagagt gcgagaaagg gcctgggtgg ggcttggacc    2340
ccggggcggg cttctggag agcccccta cgagggcctc tacggcggtg acggggtggg     2400
gggcttctgc aaaccttggt cagggaagtg gagctggctc gagtggaaga gaccacccgg    2460
```

| | |
|---|---:|
| ctcagtcggg gatgtgggag tggactgggt ggtgcagact gggggtcgag cgccttctga | 2520 |
| agtgacgggg ccgggacgcg cagggaggcg gcccaagaag cgcgccctag ccagcccag | 2580 |
| aatgcgctcg gccgcgacta ggacaacggc gggtggggct gggggcggct gccgggcggg | 2640 |
| gagcggtccc gcgccctcag ctaccccctca agagccgttg tttccctaac ttcagctgcc | 2700 |
| agaggctctg tgattggctg cggcacgatg acccgcgcac ggattggctg cttcgggccg | 2760 |
| ggggccggg cccgggggac agaatccgcc cccgaacctt caaagagggt accccccggc | 2820 |
| aggagctggc agacccagga ggtgcgacag acccgcgggg caaacggact ggggccaaga | 2880 |
| gccgggagcg cgggcgcaaa ggcaccaggg cccgcccagg gcgccgcgca gcacggcctt | 2940 |
| gggggttctg cgggccttcg ggt | 2963 |

<210> SEQ ID NO 2
<211> LENGTH: 837
<212> TYPE: DNA
<213> ORGANISM: Homo sapiens

<400> SEQUENCE: 2

| | |
|---|---:|
| tttttttct cgttttactc acaaatactt aagtatgtaa gtagatacac ttcacccaca | 60 |
| taatagagaa tactctatac atgtattcat gggtcaaagg ggtccctgag atacacacaa | 120 |
| ttcatactca tccctctgaa cactgcaagc gtcgtgtgga gccatttgct ttcccacaca | 180 |
| ctcgcttttct gccgcagcaa ggctggaccc tgctggagtg gtgatgtgca ggaactgcct | 240 |
| catagctcag gtggtaaagt tatttggctg ggaactgagt ctctcccac atgctgtcac | 300 |
| acccttcccg gccctgacaa acacaaagag atgcatccca ttgagtcacc cacttggctg | 360 |
| aaccgtgtac ctggtaaccct ccttgggagg ttctttggag ggtattttc tcctctacac | 420 |
| aaagcatgcc tgcgaagtaa gctgagaatg acaaaaacag gaaagcccaa tcttgcagag | 480 |
| acagagggc caaggcctgc atgataatgc ggcccaaatt catagctcag acccaaaaga | 540 |
| aaacaaatgt tccattcttt ctgtgtccac ctctaaacta gcaatacag tgagggcagt | 600 |
| aaattgcaat tacaagtaag aactttagca gttgctgatc ataaaatgaa aagggacaaa | 660 |
| tatgtttatc cttaacaggg tcacaaataa ttccacagct gttaattttg gcagccacga | 720 |
| ctctgcaggc agtatgggct catggtatac tatcttcatt gtcaccttgg acaaagatcc | 780 |
| tgttggccaa aggcacacag gcatcttcag gaaaactaga tttaaatggt aagatta | 837 |

<210> SEQ ID NO 3
<211> LENGTH: 498
<212> TYPE: DNA
<213> ORGANISM: Homo sapiens

<400> SEQUENCE: 3

| | |
|---|---:|
| cctatgctta tgttttaag ctccaaagac tactggttct gggaaggact gggtcactat | 60 |
| gtgaccttgt gtaggtctct tttggccctg agtccaggag ggctctgtga ctccaggttg | 120 |
| tggctgcgtc tggcagctaa caattgttta gtttacagtg tccttcctct tcatcttgtt | 180 |
| tgcattcagt tgcccatgcc tgcctctggg gggaggtggg aaggaatgtg ctcctggga | 240 |
| ggagcccagc tccatgtgcc attctgagga gccaggctgc acgcccctgg gccatagctg | 300 |
| ctggtggatg gatgagtaca ctggcagagg cactgggaag ggaagacaga attgttggcc | 360 |
| aatagtcccc ttttactgat tttcttgtca tttttgtgtt tgttttatta taaagataac | 420 |
| agctgtattt gagaaagaaa gctcaaacta taaagaaaat ttaaaattgc cctgtcttac | 480 |
| tccaactcca ttccctga | 498 |

```
<210> SEQ ID NO 4
<211> LENGTH: 1628
<212> TYPE: DNA
<213> ORGANISM: Homo sapiens

<400> SEQUENCE: 4
ctaggtgagc cagacgctgg ccttatctca tttaccatct cagagccatc tgaagggga      60 gaagggaacc gggccccagg agggagaaag tcatcaaacc tcccacatct gtgaccagcc    120
tcagtgccat acttttcta tggagggccc tgtccaatgg aactgagcac agaccagata    180
aaagaactgg gcacccagtg gcctcagtcc agggcctgga gttcaaactt tactggaaac   240
aaaggggccg agagagactg gggaaagaac tactagaaag gggctggtgc ccccatgggg   300
ctgtgggttt tggagccgcg tgcccccacc tgagcctcag ggggcccgga gtgtccacac    360
cagtggacct ttcgagaaat ggctgggcca ttgtgcagaa gaatgcccgg aaatcccgcg   420
cctccctcct ccagcaagga tggggctct tcctcctggc caggaaactc caagttggct     480
tccggagggt ggcctggggg ctgggtgcc agggacacca tcgccactgg tgggagggca    540
gggcacagcc cctccgtgtc cctttgtctc tcctgtctga aggccagagc aggctgctag   600
gcctggggcc accactgccc ctgggtgcta cacccagtgt gctgggtcac tgggaacttc   660
ctgaagtggt gtcacctgaa ctggaccccc aaggatgggg tgcgggcagt accgcaggaa   720
gaggagcagc ccctgtgaag attgagaggt ctgggaagcc cctgcggctt gggagagtgg   780
gggtcgccag gcaggggaa agcccctgtg ccaccgcttt ttgccagaga ctcaggctcc     840
agagaggcag tgagtggcat gggggggtgag gctgggggccc tgggcctgac ctccacacgc   900
ctgcctggcc tctctgtttg ccatgggatg agagagacag tgctgggact cagagcgggg   960
ctggagagtg agagtgcgag aaagggcctg ggtgggctt ggaccccggg gcgggctttc   1020
tggagagccc ccctacgagg gcctctacgg cggtgacggg gtgggggct tctgcaaacc   1080 ttggtcaggg aagtggagct ggctcgagtg gaagagacca cccggctcag tcggggatgt   1140
gggagtggac tgggtggtgc agactggggg tcgagcgcct tctgaagtga cggggccggg   1200
acgcgcaggg aggcggccca agaagcgcgc cctaggccag cccagaatgc gctcggccgc   1260
gactaggaca acggcgggtg gggctggggg cggctgccgg gcggggagcg gtcccgcgcc   1320
ctcagctacc cctcaagagc cgttgtttcc ctaacttcag ctgccagagg ctctgtgatt   1380
ggctgcggca cgatgacccg cgcacggatt ggctgcttcg ggccggggg ccgggcccgg    1440 gggacagaat ccgcccccga accttcaaag agggtacccc ccggcaggag ctggcagacc   1500
caggaggtgc gacagacccg cggggcaaac ggactggggc caagagccgg gagcgcgggc   1560
gcaaaggcac cagggcccgc ccagggcgcc gcgcagcacg gccttggggg ttctgcgggc   1620
cttcgggt                                                            1628
```

CLDN5 MINI-PROMOTERS

FIELD OF THE INVENTION

The invention relates to gene promoters and regulatory elements. More specifically, the invention relates to novel CLDN5 promoter compositions and related methods.

BACKGROUND

Claudin 5 (CLDN5) a member of the claudin family. Claudins are integral membrane proteins and components of tight junction strands. Homozygous mutant neonates gradually cease movement and die within 10 hours after birth. (Nitta et al. 2003). In the adult mouse brain, CLDN5 is expressed in all major forebrain subdivisions: the neocortex, hippocampus, basal ganglia, amygdala/basal forebrain, and olfactory bulb, as well as all other CNS regions (Maynard et al. 2003). CLDN5 is expressed in cultured mouse brain embryonic cells and in freshly isolated MBEC as early as embryonic Day 7. In situ hybridization and immunocytochemical analyses revealed the presence of the CLDN5 mRNA and its protein product in brain capillary endothelial cells, as well as in a subset of other endothelial and epithelial cells (Chen et al. 1998). In the brain and lung, immunofluorescence microscopy have shown that CLDN5 is exclusively concentrated at cell-cell borders of endothelial cells of all segments of blood vessels, but not at those of epithelial cells (Morita et al. 1999). Endothelial tight junctions are an important functional part of the formation of the blood brain barrier, and CLDN5 has been shown to be a critical determinant of blood brain barrier permeability (Matter and Balda 2003; Nitta et al. 2003; Stamatovic et al. 2008).

Functional mouse CLDN5 promoter sequences have been identified and analyzed (Burek and Forster 2009). In this paper, the authors perform luciferase reporter assays in a brain microvascular endothelial cell line, but do not report any in vivo expression data. A 1.5 kb huma CLDN5 promoter sequence was tested for expression in bovine retinal endothelial cells (Felinski et al. 2008).

There exists a significant need for minimal human promoter elements which are capable of driving expression in specific cell types and/or in specific regions of the brain. Identification of minimal elements required for adequate expression and specificity will allow ease of use in expression constructs.

SUMMARY OF THE INVENTION

The present invention provides novel nucleic acid compositions and methods relating to CLDN5 promoters having a sequence other than a native CLDN5 promoter.

In one embodiment of the invention, there is provided an isolated nucleic acid fragment comprising a CLDN5 mini-promoter, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or SEQ ID NO: 3. The CLDN5 basal promoter may have a nucleic acid sequence which is substantially similar in sequence and function to SEQ ID NO: 4. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a CLDN5 mini-promoter element, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or SEQ ID NO: 3. The CLDN5 basal promoter may have a nucleic acid sequence which is substantially similar in sequence and function to SEQ ID NO: 4. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell a expression vector comprising a CLDN5 mini-promoter element, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or SEQ ID NO: 3. The CLDN5 basal promoter may have a nucleic acid sequence which is substantially similar in sequence and function to SEQ ID NO: 4. Cells useful in such methods are permissive for expression of a sequence operably linked to a CLDN5 mini-promoter described herein, and include without limitation blood vessel cells in the brain. Retinal cells of neural or neuroglial origin are of particular interest for expression, e.g. retinal ganglion cells, retinal bipolar interneuron cells, etc. In such methods the CLDN5 mini-promoter is operably linked to an expressible sequence, e.g. reporter genes, genes encoding a polypeptide of interest, regulatory RNA sequences such as miRNA, siRNA, anti-sense RNA, etc.; and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or SEQ ID NO: 3. The CLDN5 basal promoter may have a nucleic acid sequence which is substantially similar in sequence and function to SEQ ID NO: 4. In some embodiments, the cell is a blood vessel cell in the brain. In some embodiments, the cell is a retinal cell, such as neural retinal cell or a neuroglial retinal cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene; and 2) detecting the expression of the reporter gene in the progeny of the cell as a means of determining the lineage, identity or developmental state of the progenitor cell or progeny thereof. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or SEQ ID NO: 3. The CLDN5 basal promoter may have a nucleic acid sequence which is substantially similar in sequence and function to SEQ ID NO: 4. In some embodiments, the cell may be a blood vessel cell of the brain. In some embodiments, the cell may be a retinal cell, such as retinal ganglion cell, retinal bipolar cell.

In certain embodiments of the invention, there is thus provided a method of treatment of a subject having a disease or condition of the eye, including the retina, the method comprising administering to the subject a therapeutically effective dose of a composition comprising a CLDN5 mini-promoter element, wherein the CLDN5 mini-promoter element comprises one or more CLDN5 regulatory elements operably linked in a non-native conformation to a CLDN5 basal promoter element and to a sequence for which expression in the retina is desired. The CLDN5 mini-promoter element may have a nucleic acid sequence substantially similar in sequence and function to SEQ ID NO: 1. The CLDN5 regulatory element may have a nucleic acid sequence substantially similar in sequence and function to SEQ ID NO: 2 or SEQ ID NO: 3. The CLDN5 basal promoter element may have a nucleic acid sequence substantially similar in sequence and function to SEQ ID NO: 4. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

DETAILED DESCRIPTION

The compositions of the present invention include novel polynucleotides comprising CLDN5 promoter elements (also referred to herein as CLDN5 mini-promoters) as well as novel expression vectors comprising said CLDN5 promoter elements (or mini-promoters). The present invention also includes various methods utilizing these novel CLDN5 promoter (or mini-promoter) elements or expression vectors.

The term 'CLDN5' refers to the gene which encodes the CLDN5 protein, also referred to as AWAL, BEC1, CPETRL1, TMVCF, and also as MBEC1 in mouse. The human homolog of CLDN5 is encoded by the human gene identified as EntrezGene #7122, and is located at chromosomal location 22q11.21. The protein encoded by human CLDN5 has the Protein Accession #O00501.1 and/or Q53HW4 (Swiss-Prot). Other mammalian CLDN5 homologs include but are not limited to: *Rattus norvegicus* (EntrezGene #65131, Protein Accession # Q9JKD6.2), *Mus musculus* (EntrezGene #12741, Protein Accession #O54942.2).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. An 'CLDN5 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 4. The basal promoter may be truncated relative to SEQ ID NO:4, e.g. by a deletion of about 10, 20, 30 40, 50, 75, 100, or more nucleotides at either terminus.

A promoter may also include one or more 'regulatory elements' which may also influence the expression or transcription by the promoter. Such regulatory elements encode specific DNA sequences which bind other factors, which may include but are not limited to enhancers, silencers, insulators, and/or boundary elements. An 'CLDN5 regulatory element', in the context of the present invention and as used herein, may be a nucleic acid compound having a sequence with at least 65%, at least 70%, at least 80%, at least 85%, at least 90%, at least 95%, or at least 99% similarity to SEQ ID NO: 2 or 3. The regulatory sequence may be truncated relative to SEQ ID NO:2 or SEQ ID NO:3, e.g. by a deletion of about 10, 20, 30 40, 50, 75, 100, or more nucleotides at either terminus.

The present invention provides, in certain embodiments as described herein, different promoters of the CLDN5 gene. In some embodiments, the CLDN5 promoter comprises one or more CLDN5 regulatory elements operably linked to a CLDN5 basal promoter. In certain embodiments, the CLDN5 regulatory elements are directly joined with no intervening sequences. In other embodiments, the CLDN5 regulatory elements may be operably linked with intervening sequences. In general the spacing between the regulatory elements is not more than about 15 KB, generally not more than about 10 KB, usually not more than about 1 KB, more often not more than about 500 nt, and may be not more than about 100 nt, down to a direct joining of the two sequences.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence.

Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene between the identified elements may be partially or completely removed. Other non-native sequences may optionally be inserted between the identified promoter elements. The term mini-promoter may also refer to a minimal promoter element in a native conformation which is capable of driving protein expression, but which has had non-essential elements removed in order to reduce its size. A mini-promoter may provide certain advantages over larger promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters would be apparent to one of skill in the art. In some embodiments of the invention, there are thus provided novel CLDN5 mini-promoters comprising one or more CLDN5 regulatory elements operably linked in a non-native conformation to a CLDN5 basal promoter. In general the spacing between the one or more CLDN5 regulatory elements and the CLDN5 basal promoter is not more than about 15 KB, generally not more than about 10 KB, usually not more than about 1 KB, more often not more than about 500 nt, and may be not more than about 100 nt, down to a direct joining of the two sequences.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (i.e. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and/or regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. The original promoter sequence can be truncated, e.g. by a deletion of about 10, 20, 30 40, 50, 75, 100, or more nucleotides at either terminus. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which is may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, JoIm Wiley and Sons.

In certain embodiments of the invention, there are provided methods of treatment using the nucleic acids or expression vectors, for instance for gene therapy applications. The nucleic acids or expression vectors of the present invention may be administered in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, attenuated virus, adeno-associated virus (AAV), and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenously, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

The term "retinal cell", as used herein may refer to any cell present in the retina of an animal, e.g. a mammal. "Mammal" refers to any animal classified as a mammal, including humans, domestic and farm animals, and zoo, sports, or pet animals, such as dogs, horses, cats, cows, sheep, goats, pigs, etc. Preferably, the mammal is human. Within the class of retinal cells, retinal cells of neural type are of particular interest, for example retinal ganglion cells and retinal bipolar interneuron cells. Other neural retinal cells may include, without limitation, amacrine cells, photoreceptors (rods/cones), horizontal cells, etc. Neuroglial retinal cells are also of interest, for example Muller cells, astroglial cells, etc.

CLDN5 Promoters

The present invention herein provides novel CLDN5 mini-promoter sequences which are capable of effecting transcriptional expression in a spatial and temporal fashion which may be similar to naturally occurring CLDN5 promoters, although the invention may also provide for variation away from the native expression patterns. In some embodiments, the CLDN5 mini-promoters of the invention comprise CLDN5 promoter elements joined in a non-native configuration, thus providing advantageous characteristics. In other embodiments, the CLDN5 mini-promoters comprise basal promoters with advantageous characteristics. Also provided are novel expression vector compositions comprising CLDN5 mini-promoters which allow consistent specific spatiotemporal transcription of expression sequences. Also provided are novel methods utilizing these CLDN5 mini-promoters and expression vectors.

The CLDN5 mini-promoters of some embodiments of the invention, as described herein, comprise CLDN5 promoter elements that are joined by non-native sequences. In this context, the native intervening sequences may have been partially or completely removed, and optionally may have been replaced with non-native sequences. In such a fashion, the natural spacing of the promoter elements, for instance the human CLDN5 regulatory elements corresponding to SEQ ID NO: 2 and/or 3 and the human CLDN5 basal promoter element corresponding to SEQ ID NO: 4, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications.

The inventors have provided, as an illustrative non-limiting Working Example, a human CLDN5 mini-promoter having a sequence corresponding to SEQ ID NO: 1 capable of directing expression of an expressible sequence which is operably linked downstream of the CLDN5 mini-promoter in specific cell types in different regions of the brain and eye. The CLDN5 regulatory elements (SEQ ID NOs: 2 and 3) and CLDN5 basal promoter element (SEQ ID NO: 4) have sequences which are identical to those found upstream of the human CLDN5 gene, however the promoter has been miniaturized from the native promoter by removal of endogenous intervening sequences.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified mini-promoter provide for a transcription rate of an expressible sequence operably linked to a modified promoter sequence that is at least about 75% the transcription rate of the promoter sequence of SEQ ID NO:1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

In one embodiment of the invention, there is provided an isolated nucleic acid fragment comprising a CLDN5 mini-promoter, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or 3. The CLDN5 basal promoter may have a nucleic acid sequence which is substantially similar in sequence and function to SEQ ID NO: 4. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

It is an object of the present invention to provide means of expressing a gene, protein, RNA interference molecule or the like in a cell, tissue or organ. As such, the inventors thus provide novel expression vectors comprising CLDN5 mini-promoters which are capable of accomplishing this task. In one embodiment, there is provided an expression vector comprising a CLDN5 mini-promoter element, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or 3. The CLDN5 basal promoter may have a nucleic acid sequence which is substantially similar in sequence and function to SEQ ID NO: 4. The CLDN5 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

The inventors have herein provided expression vectors comprising novel CLDN5 mini-promoter elements that are capable of directing transcription of an expression sequence in specific cell types in specific regions of the brain and body, most notably the blood vessels in the brain and in retinal cells of the eye. In some embodiments of the invention, there is thus provided a method for expressing a gene, protein, RNA interference molecule or the like in the targeted cells of the brain. In another embodiment there is provided a method for expressing a gene, protein, RNA interference molecule or the like in targeted cells of the eye, for instance retinal ganglion cells, or retinal bipolar cells. In one embodiment, there is provided a method for expressing a gene, protein, RNA interference molecule or the like in a cell, the method comprising introducing into the cell a expression vector comprising a CLDN5 mini-promoter element, wherein the CLDN5 mini-promoter comprises one or more CLDN5 regulatory elements operably linked in a non-native conformation to a CLDN5 basal promoter. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or 3. The CLDN5 basal promoter may have a nucleic acid sequence which is substantially similar in sequence and function to SEQ ID NO: 4.

Cells of interest include blood vessel cells in the brain. Cells of interest include retinal cells, such as retinal ganglion cells or retinal bipolar cells. The CLDN5 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or 3. The CLDN5 basal promoter may have a nucleic acid sequence which is substantially similar in sequence and function to SEQ ID NO: 4. In some embodiments, the cell is a blood vessel cell in the brain. In some embodiments, the cell is a retinal cell, such as a retinal ganglion cell or a retinal bipolar cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a CLDN5 mini-promoter element operably linked to an expressible sequence, wherein the CLDN5 mini-promoter element comprises one or more CLDN5 regulatory elements operably linked in a non-native conformation to a CLDN5 basal promoter element, and wherein the expressible sequence comprises a reporter gene; and 2) detecting the expression of the reporter gene in the progeny of the cell as a means of determining the lineage, identity or developmental state of the progenitor cell or progeny thereof. The CLDN5 mini-promoter may have a nucleic acid sequence which is substantially similar in sequence and function to SEQ ID NO: 1. The one or more CLDN5 regulatory elements may have nucleic acid sequences which are substantially similar in sequence and function to SEQ ID NO: 2 or 3. The CLDN5 basal promoter may have a nucleic acid sequence which is substantially similar in sequence and function to SEQ ID NO: 4. In some embodiments, the cell may be a blood vessel cell of the brain. In some embodiments, the cell may be a retinal cell, such as a retinal ganglion cell or a retinal bipolar cell.

The inventors have herein illustrated that certain CLDN5 mini-promoter elements of the present invention are capable of driving expression in retinal cells such as retinal ganglion cells or retinal bipolar cells. This provides additional unexpected methods of use for these mini-promoter elements. For instance, it may be desirable to utilize the CLDN5 mini-promoters of the present invention in a gene therapy or cell therapy application wherein the CLDN5 mini-promoters are utilized to drive expression of a therapeutic or beneficial compound, such as a protein, in retinal ganglion or retinal bipolar cells. In such a way, the therapeutic or beneficial compound may be useful for a disease or condition that involves such retinal cells, or which may be improved by expression of the therapeutic or beneficial compound in those cells. In certain embodiments of the invention, there is thus provided a method of treatment of a subject having a disease or condition of the eye, the method comprising administering to the subject a therapeutically effective dose of a composition comprising a CLDN5 mini-promoter element, wherein the CLDN5 mini-promoter element comprises one or more CLDN5 regulatory elements operably linked in a non-native conformation to a CLDN5 basal promoter element. The CLDN5 mini-promoter element may have a nucleic acid sequence substantially similar in sequence and function to SEQ ID NO: 1. The CLDN5 regulatory element may have a nucleic acid sequence substantially similar in sequence and function to SEQ ID NO: 2 or 3. The CLDN5 basal promoter element may have a nucleic acid sequence substantially similar in sequence and function to SEQ ID NO: 4. The disease or condition may be chosen from: retinal diseases, retinal degeneration, retinal damage, blindness, macular degeneration, retinitis pigmentosa, inherited retinal genetic diseases, diabetic retinopathy, cone rod dystrophy, hypertensive/diabetic retinopathy. The therapeutic or beneficial compound may be a light-sensitive compound, for instance rhodopsin, channel rhodopsin, etc.

The inventors herein further describe the present invention by way of the following non-limiting examples:

EXAMPLE 1

The following methods are used to obtain retinal expression of a sequence operably linked to a CLDN5 mini-promoter of the present invention.

General Methods

Figure 1:
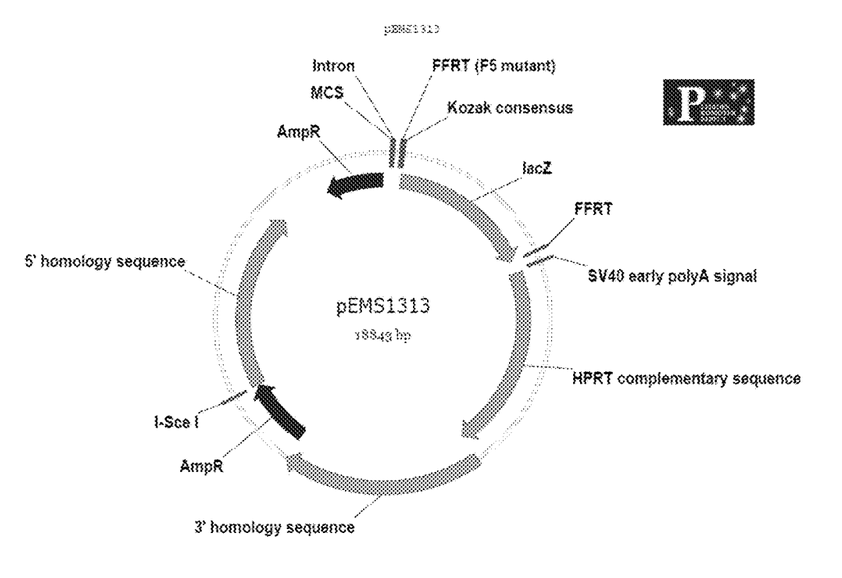
FIG. 1: Vector diagram of backbone pEMS1313

Expression Vector. The nucleic acid fragment corresponding to SEQ ID NO: 1 is inserted into the multiple cloning site of the pEMS1313 (see FIG. 1) to produce the expression vectors used in the experiments.

Derivation of mEMS1202 Embryonic Stem Cells. Blastocysts are obtained from natural mating of B6-Hprt1$^{b-m3}$ homozygous females to 129-ROSA26 heterozygous males at 3.5 dpc. Blastocysts are flushed from uterine horns as per Hogan et al. (1994), cultured in EmbryoMax® KSOM with ½ Amino Acids, Glucose and Phenol Red (Cat # MR-121, Millipore/Chermicon, Temecula, Calif.) for 3-5 h, and then transferred onto mitomycin C (mitC; Cat#M4287, Sigma, Oakville, ON) mitotically inactivated B6-Hprt1$^{b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media is replaced 3-5 hour prior to transfer).

Blastocysts are cultured as per (Cheng et al. 2004) with the following modifications: Cells are cultured for 7-9 days in KSR-ESC with minimal disturbance (check on day 2 to determine if the blastocysts have 'hatched' out of the zona pellucida) and no media changes. Blastocysts which hatch and have a well developed ICM (inner cell mass) are treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media is replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON) and 0.01% β-mercaptoethanol (Sigma, Oakville, ON)) in 25%, 50%, 75% proportions (respectively) to adapt the cells to FBS containing media.

On day 7 the cells are trypsinized to one well of a 24 well plate containing 1 ml of 100% FBS-ESC media, with daily media replacement. Once confluent, wells containing ESC colonies are expanded 3×24 wells (with MEFs), then passaged to 3×24 (with MEFs) and 3×12 well (plastic—no MEFs) for DNA analysis. Once confluent, the 3×24 wells are combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures are genotyped for X & Y chromosomes (Clapcote and Roder 2005), Gt(ROSA)26Sor$^{tm1Spr}$ and WT alleles and Hprt1$^{b-m3}$ and WT alleles. B6129F1-Gt(ROSA) 26Sor$^{tm1Sor}$/+, Hprt1$^{b-m3}$/Y (mEMS1204 series) and B6129F1-Gt(ROSA)26Sor$^{tm1Sor}$+/+, Hprt1$^{b-m3}$/Y (mEMS1202 series) cell lines are identified.

Knock-In at the Hprt1 Locus.

The CLDN5 expression vector plasmid DNA is purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA is resuspended in 85 µl of TE (10:0.1) to a final concentration of 187.5 ng/µl. mEMS1202 ESCs are grown to confluence on 4-6 T75 flasks of mitC treated Hprt1$^{b-m3}$ mouse embryonic feeders (MEFs) in FBS-ESC media. ESCs (1.7-2.5×10$^7$) in 720 µl 1×PBS are added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants are selected for using HAT media (FBS-ESC media containing 1× HAT ((0.1 mM sodium hypoxanthine, 0.4 mM aminopterin, 0.16 mM thymidine), Cat#21060-017, Invitrogen, Burlington, ON). HAT media is changed every day for the first 3 days, and then every 3$^{rd}$ day thereafter, for up to 10 days. Individual colonies are counted and, typically, no more than 2 isolated colonies are picked per 100 mm dish to optimize for independent homologous recombination events. These colonies are expanded under standard protocols for verification of the desired recombination event.

Derivation of Knock-in Mice. Chimeric mice from targeted ESCs are generated by microinjection (Hogan et al. 1994) into E3.5 blastocysts followed by implantation into the uterine horns of 2.5 day pseudopregnant ICR females. Chimeras are identified and coat color chimerism determined as outlined below.

Male chimeras derived from the mEMS1202 cell lines are mated with B6-Alb females, and germline transmission identified by the presence of the dominant Tyr$^+$ (tyrosinase; wild type) and the A$^W$ (nonagouti; white bellied agouti) or a (nonagouti; nonagouti) alleles making the progeny appear brown with a cream belly or black, respectively. Non-germline progeny are homozygous for the recessive Tyr$^{c-2J}$ (tyrosinase; albino 2 Jackson) allele and appear white. All germline female offspring should carry the knock-in X Chromosome and are mated with B6 males. N2 offspring are analyzed for the presence of the KI allele by PCR.

Determination of Coat Color Chimerism. mEMS1202-derived chimeras are identified and level of coat color chimerism determined as follows. mEMS1202 ESCs, heterozygous A$^W$/a and homozygous for the wild type Tyr$^+$ alleles will produce chimeras with agouti and black patches on a white background when injected into B6-Alb blastocysts. The agouti patches result from melanocytes derived solely from the ESCs (A$^W$/a, Tyr$^+$/Tyr$^+$), whereas 'black' patches result from melanocytes that are a mixture of ESC (A$^W$/a, Tyr$^+$/Tyr$^+$) and host (a/a, Tyr$^{c-2J}$/Tyr$^{c-2J}$). For E14TG2a injections into B6 and mEMS1202 injections into B6-Alb, overall chimerism is calculated by summing the percent of coat color patches derived solely from the ESC, plus half the percent of the ESC+host areas, where we conservatively estimate that half the melanocytes derive from the ESC and half from the host.

Reporter Gene Detection. Adult male hemizygous Mini-Promoter and age matched control mice are perfused with 4% paraformaldehyde (PFA) as previously described (Young, Berry et al. 2002). Whole brains and eyes are dissected out and post-perfusion immersion fixed with PFA for 2 hours at 4° C. The brains are sectioned using a coronal or sagittal brain mold (Electron Microscopy Sciences) at 1 mm and sections were placed in 12-well tissue culture plates. One whole eye and one half-cut eye, using a razor-blade, are also placed in the plate. LacZ expression is detected by using 5-bromo-4-chloro-3-indolyl-β-D-galactopyranoside (X-Gal) as the substrate. The X-Gal staining solution contains the following: 1.0 mg/ml X-Gal, 2 mM potassium ferricyanide, 2 mM potassium ferrocyanide, and 40 mM MgCl2 in PBS.

In brief, brain sections are rinsed with phosphate buffered saline (PBS), then incubated with X-Gal (Boeringer Mannheim, Indianapolis, Ind.) at 37° C., usually overnight. After staining the tissue is rinsed with PBS and moved into PBS containing 0.02% azide for storage. Eyes are further processed by post-fixing with 4% PFA for 2 hours at room temperature. After fixation, eyes are rinsed with PBS and cryoprotected in 25% sucrose-PBS at 4° C. overnight. Eyes are removed from the solution and blotted with a KimWipe before embedment in Optimal Cutting Temperature (OCT) alongside positive and negative controls. 12 µm sections were taken using a Microm HM 550 cryostat and directly mounted onto SuperFrost Plus microscope slides. Bright field images are taken on a Leica MZ125 dissecting microscope and photographed using an Olympus Coolsnap cf color camera with the ImagePro software package.

EXAMPLE 2

Expression of Reporter by CLDN5 Promoter Elements

Using the above methods, the CLDN5 DNA expression vectors comprising the CLDN5 promoter element corresponding to SEQ ID NO: 1 (regulatory regions corresponding to SEQ ID NO: 2 and 3 fused to basal promoter SEQ ID NO: 4) are introduced into mouse embryonic stem cells (ESCs) at the HPRT locus. The ESCs are used to generate genetically modified mice containing CLDN5 mini-promoters. Immunohistochemical and immunofluorescence analysis of mouse brain and eye tissue slices are assessed for expression in the blood vessels throughout the brain and also in spinal cord; and expression in certain cells of the eye, including retinal ganglion cells or retinal bipolar cells. Evidence of expression in retinal bipolar cell in the mouse eye can be determined by X-gal staining.

Detection of cell bodies located in the inner nuclear layer of the retina with processes extending all the way to the retinal ganglion cell layer is indicative of expression in retinal bipolar cells or retinal ganglion cells.

REFERENCES

Bronson, S. K., E. G. Plaehn, et al. (1996). "Single-copy transgenic mice with chosen-site integration." *Proc Natl Acad Sci USA* 93(17): 9067-72.

Burek, M. and C. Y. Forster (2009). "Cloning and characterization of the murine claudin-5 promoter." *Mol Cell Endocrinol* 298(1-2): 19-24.

Chen, Z., M. Zandonatti, et al. (1998). "Brain capillary endothelial cells express MBEC1, a protein that is related to the *Clostridium perfringens* enterotoxin receptors." *Lab Invest* 78(3): 353-63.

Cheng, J., A. Dutra, et al. (2004). "Improved generation of C57BL/6J mouse embryonic stem cells in a defined serum-free media." *Genesis* 39(2): 100-4.

Clapcote, S. J. and J. C. Roder (2005). "Simplex PCR assay for sex determination in mice." *Biotechniques* 38(5): 702, 704, 706.

Felinski, E. A., A. E. Cox, et al. (2008). "Glucocorticoids induce transactivation of tight junction genes occludin and claudin-5 in retinal endothelial cells via a novel cis-element." *Exp Eye Res* 86(6): 867-78.

Hogan, B., R. Beddington, et al. (1994). *Manipulating the mouse*. Cold Spring Harbor, Cold Spring Harbor Laboratory Press.

Hooper, M., K. Hardy, et al. (1987a). "HPRT-deficient (Lesch-Nyhan) mouse embryos derived from germline colonization by cultured cells." *Nature* 326(6110): 292-5.

Hooper, M., K. Hardy, et al. (1987b). "HPRT-deficient (Lesch-Nyhan) mouse embryos derived from germline colonization by cultured cells." *Nature* 326: 292-295.

Jasin, M., M. E. Moynahan, et al. (1996). "Targeted transgenesis." *Proc Natl Acad Sci USA* 93(17): 8804-8.

Lee, K. H., C. K. Chuang, et al. (2007). "An alternative simple method for mass production of chimeric embryos by coculturing denuded embryos and embryonic stem cells in Eppendorf vials." *Theriogenology* 67(2): 228-37.

Liu, L., E. E. Geisert, et al. (2007). "A transgenic mouse class-III beta tubulin reporter using yellow fluorescent protein." *Genesis* 45(9): 560-9.

Matter, K. and M. S. Balda (2003). "Holey barrier: claudins and the regulation of brain endothelial permeability." *J Cell Biol* 161(3): 459-60.

Maynard, T. M., G. T. Haskell, et al. (2003). "A comprehensive analysis of 22q11 gene expression in the developing and adult brain." *Proc Natl Acad Sci USA* 100(24): 14433-8.

Morita, K., H. Sasaki, et al. (1999). "Endothelial claudin: claudin-5/TMVCF constitutes tight junction strands in endothelial cells." *J Cell Biol* 147(1): 185-94.

Nitta, T., M. Hata, et al. (2003). "Size-selective loosening of the blood-brain barrier in claudin-5-deficient mice." *J Cell Biol* 161(3): 653-60.

Ponchio, L., L. Duma, et al. (2000). "Mitomycin C as an alternative to irradiation to inhibit the feeder layer growth in long-term culture assays." *Cytotherapy* 2(4): 281-6.

Stamatovic, S. M., R. F. Keep, et al. (2008). "Brain endothelial cell-cell junctions: how to "open" the blood brain barrier." *Curr Neuropharmacol* 6(3): 179-92.

van der Weyden, L., D. J. Adams, et al. (2002). "Tools for targeted manipulation of the mouse genome." *Physiol Genomics* 11(3): 133-64.

Young, K. A., M. L. Berry, et al. (2002). "Fierce: a new mouse deletion of Nr2e1; violent behaviour and ocular abnormalities are background-dependent." *Behav Brain Res* 132(2): 145-58.

What is claimed is:

1. An isolated polynucleotide comprising a CLDN5 mini-promoter wherein the CLDN5 mini-promoter sequence consists of the nucleotide sequence of SEQ ID NO: 1.

2. The isolated polynucleotide of claim 1, operably linked to an expressible sequence.

3. A vector comprising the isolated polynucleotide of claim 1.

4. A cell comprising the vector of claim 3.

5. The cell of claim 4, wherein the vector is stably integrated into the genome of the cell.

6. The cell of claim 4, wherein the cell is a stem cell or a retinal cell.

7. A method of expressing a sequence of interest, the method comprising operably linking the sequence of interest to the polynucleotide of claim 1; and introducing the sequence of interest linked to the polynucleotide into a cell permissive for expression from the CLDN5 mini-promoter.

* * * * *